US006686337B2

(12) United States Patent
Connor

(10) Patent No.: US 6,686,337 B2
(45) Date of Patent: Feb. 3, 2004

(54) COMBINATION THERAPY COMPRISING ANTI-DIABETIC AND ANTICONVULSANT AGENTS

(75) Inventor: Gregory S. Connor, Tulsa, OK (US)

(73) Assignee: Ortho-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 10/042,425

(22) Filed: Oct. 25, 2001

(65) Prior Publication Data

US 2002/0147157 A1 Oct. 10, 2002

Related U.S. Application Data

(60) Provisional application No. 60/244,225, filed on Oct. 30, 2000.

(51) Int. Cl.[7] .................. A01N 43/04; A01N 46/16; A61K 31/70; A61K 31/35
(52) U.S. Cl. .................. 514/23; 514/454; 514/601
(58) Field of Search .................. 514/23, 454, 601

(56) References Cited

U.S. PATENT DOCUMENTS

| 4,513,006 | A |   | 4/1985 | Maryanoff et al. |
| 5,242,942 | A |   | 9/1993 | Costanzo et al. |
| 5,384,327 | A |   | 1/1995 | Costanzo et al. |
| 5,387,700 | A |   | 2/1995 | Maryanoff et al. |
| 6,071,537 | A | * | 6/2000 | Shank .................. 424/464 |
| 6,130,216 | A | * | 10/2000 | Antonucci et al. ....... 514/252.1 |
| 6,191,163 | B1 |   | 2/2001 | Cottrell |

FOREIGN PATENT DOCUMENTS

| WO | WO 99/44581 A2 | 9/1999 |
| WO | WO 00/50020 A2 | 8/2000 |
| WO | WO 00/59506 A1 | 10/2000 |
| WO | WO 00/61139 A1 | 10/2000 |
| WO | WO 00/61140 A1 | 10/2000 |
| WO | WO 00/76493 A1 | 12/2000 |
| WO | WO 01/27128 A1 | 4/2001 |

OTHER PUBLICATIONS

Marks,Jennifer B., MD, The Insulin Resistance Syndrome, The Monitor, vol. 1, No. 3, Spring 1996.*
PCT Search Report for PCT/US 01/50840 dated Nov. 13, 2002.
Osborne et al, Topiramate Improves Glycemic Control and Triglycerides in Animal Models. Presented to ADA. Abstracts published on line http://www.diabetes.org/am01/AnnualMeeting/Abstracts/AbstractSearch.asp pp 1–11 Abstract.
Demarest, K. et al Topiramate Improves Tolerance and May Improve Insulin Sensitivity in Animal Models of Type 2 Diabetes Mellitus. pp. 1–10. Abstract.
Demarest Poster 6 pages Figure 1a to Figure 4.
Crooke et al. Abstract, Topiramate Improves Glycemic Control Independent of Weight Loss in ob/ob Mice 1 page.
Demarest et al Abstract Topiramate Improves Glucose Tolerance and May Improve Insulin Sensitivity in Animal Models of Type 2 Diabetes Mellitus 1 page.
Osborne et al Abstract Topiramate Improves Glycemic Control and Triglycerides in Animal Models 1 page The Posters were presented at the Amierican Diabetes Association Conference held Jun. 22–26 in Philadelphia.
Smith, Ulf et al, Topiramate, a novel antiepileptic drug, reduces body weight and food intake in obesity. 1 page Published in Obesity Research vol. 8 (Suppl. 1) Oct. 2000.

* cited by examiner

Primary Examiner—James O. Wilson
Assistant Examiner—Traviss C. McIntosh, III

(57) ABSTRACT

Combination therapy comprising anti-diabetic agents and anticonvulsant derivatives useful for the treatment of Type II diabetes mellitus and Syndrome X are disclosed.

12 Claims, No Drawings

COMBINATION THERAPY COMPRISING ANTI-DIABETIC AND ANTICONVULSANT AGENTS

CROSS REFERENCE TO RELATED APPLICATION

This application claims priority from U.S. provisional application Serial No. 60/244,225 filed Oct. 30, 2000, the contents of which are hereby incorporated by reference.

BACKGROUND OF THE INVENTION

Type II (or Type 2) diabetes mellitus (non-insulin-dependent diabetes mellitus or NIDDM) is a metabolic disorder involving dysregulation of glucose metabolism and insulin resistance, and long-term complications involving the eyes, kidneys, nerves, and blood vessels. Type II diabetes mellitus usually develops in adulthood (middle life or later), although it is increasingly reported in adolescents. It is described as the body's inability to make either sufficient insulin (abnormal insulin secretion) or its inability to effectively use insulin (resistance to insulin action in target organs and tissues). More particularly, patients suffering from Type II diabetes mellitus have a relative insulin deficiency. That is, in these patients, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension. These micro-and macro-vascular complications can lead to blindness, end-stage renal disease, limb amputation and myocardial infarction.

Syndrome X, is also termed Insulin Resistance Syndrome (IRS), Metabolic Syndrome, or Metabolic Syndrome X. It is a disorder that presents risk factors for the development of Type II diabetes mellitus and cardiovascular disease including glucose intolerance, hyperinsulinemia and insulin resistance, dyslipidemia (eg, high triglycerides and low HDL-cholesterol), hypertension and obesity.

Typical treatment of Type II diabetes mellitus and Syndrome X focuses on maintaining the blood glucose level as near to normal as possible and includes diet and exercise, and when necessary, treatment with anti-diabetic agents, insulin or a combination thereof. TYPE II diabetes that cannot be controlled by dietary management is treated with oral anti-diabetic agents including, but not limited to, sulfonylureas (e.g., not limited to first generation: chlorpropamide, tolazamide, tolbutamide; second generation: glyburide, glipizide; and third generation: glimepiride), biguanides (e.g., metformin), thiazolidinediones (e.g., rosiglitazone, pioglitazone, troglitazone), alpha-glucosidase inhibitors (e.g., acarbose, miglitol), meglitinides (e.g., repaglinide), other insulin-sensitizing compounds, and/or other anti-obesity agents (e.g., orlistat or sibutramine). For Syndrome X, the anti-diabetic agents are additionally combined with pharmacological agents for the treatment of the concomitant co-morbidities (e.g., antihypertensives for hypertension, hypolipidemic agents for hyperlipidemia).

First-line therapies typically include metformin and sulfonylureas as well as thiazolidinediones. Metformin monotherapy is a first line choice, particularly for treating Type II diabetic patients who are also obese and/or dyslipidemic. Lack of an appropriate response to metformin is often followed by treatment with metformin in combination with sulfonylureas, thiazolidinediones, or insulin. Sulfonylurea monotherapy (including all generations of drugs) is also a common first line option. Another first line therapy choice may be thiazolidinediones. Patients who do not respond appropriately to oral anti-diabetic monotherapy, are given combinations of these agents. When glycemic control cannot be maintained with oral antidiabetics alone, insulin therapy is used either as a monotherapy, or in combination with oral antidiabetic agents. These same strategies, optionally in combination with additional strategies (e.g., antihypertensive) can be used for the treatment of Syndrome X.

Anti-diabetic agents include, but are not limited to:

(a) Sulfonylureas, which increase insulin production by stimulating pancreatic beta cells, and therefore act as insulin secretagogues. The primary mechanism of action of sulfonylureas is to close ATP-sensitive potassium channels in the beta-cell plasma membrane, initiating a chain of events that result in insulin release. Suitable examples of sulfonylureas include, but are not limited to chlorpropamide, tolazamide, tolbutamide, glyburide, glipizide, glimepiride, and like.

(b) Meglitinides, another class of insulin secretagogues, that have a mechanism of action distinct from that of the sulfonylureas. Suitable examples of meglitinides include, but are not limited to repaglinide.

(c) Agents which modify insulin secretion such as Glucagon-like Peptide-1(GLP-1) and it's mimetics, Glucose-insulinotropic peptide (GIP) and it's mimetics, Exendin and it's mimetics, and Dipeptyl Protease Inhibitors (DPPIV).

(d) Biguanides which decrease liver glucose production and increase the uptake of glucose. Suitable examples include, but are not limited to metformin.

(e) Thiazolidinediones, insulin sensitizing drugs which decrease peripheral insulin resistance by enhancing the effects of insulin at target organs and tissues. These drugs bind and activate the nuclear receptor, peroxisome proliferator-activated receptor-gamma (PPAR-gamma) which increases transcription of specific insulin-responsive genes. Suitable examples of PPAR-gamma agonists are the thiazolidinediones which include, but are not limited to rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, and the like. Additionally, the non-thiazolidinediones also act as insulin sensitizing drugs, and include, but are not limited to GW2570, and the like.

(f) Retinoid-X receptor (RXR) modulators, also insulin sensitizing drugs, which include, but are not limited to targretin, 9-cis-retinoic acid, and the like.

(g) Other insulin sensitizing agents include, but are not limited to INS-1, PTP-1B inhibitors, GSK3 inhibitors, glycogen phosphorylase a inhibitors, fructose-1,6-bisphosphatase inhibitors, and the like.

(h) Alpha-glucosidase inhibitors which act to inhibit alpha-glucosidase. Alpha-glucosidase converts fructose to glucose, thus these inhibitors delay the digestion of carbohydrates. The undigested carbohydrates are subsequently broken down in the gut, thereby reducing the post-prandial glucose peak. Suitable examples include, but are not limited to, acarbose and miglitol.

(i) Insulins, including regular or short-acting, intermediate-acting, and long-acting insulins, inhaled insulin and insulin analogues such as insulin molecules with minor differences in the natural amino acid sequence. These modified insulins may have faster onset of action and/or shorter duration of action.

(j) Small molecule mimics of insulin, including, but not limited to L-783281, TE-17411, and the like.

(k) Na-glucose co-transporter inhibitors which inhibit the renal reabsorption of glucose such as T-1095, T-1095A, phlorizen, and the like.

(l) Amylin agonists which include, but are not limited to pramlintide, and the like.

(k) Glucagon antagonists such as AY-279955, and the like.

In addition to antidiabetic agents, therapies may include add-on treatment with anti-obesity agents such as orlistat, a pancreatic lipase inhibitor, which prevents the breakdown and absorption of fat; or sibutramine, an appetite suppressant and inhibitor of the reuptake of serotonin, norepinephrine and dopamine in the brain. Other potential add-on anti-obesity agents include, but are not limited to, appetite-suppressants acting through adrenergic mechanisms such as benzphetamine, phenmetrazine, phentermine, diethylpropion, mazindol, sibutramine, phenylpropanolamine or, ephedrine; appetite-suppressant agents acting through serotonergic mechanisms such as quipazine, fluoxetine, sertraline, fenfluramine, or dexfenfluramine; appetite-suppressant agents acting through dopamine mechanisms, eg, apomorphine; appetite-suppressant agents acting through histaminergic mechanisms (eg, histamine mimetics, H3 receptor modulators); enhancers of energy expenditure such as beta-3 adrenergic agonists and stimulators of uncoupling protein function; leptin and leptin mimetics; neuropeptide Y antagonists; melanocortin-1, 3 and 4 receptor modulators; cholecystokinin agonists; glucagon-like peptide-1 (GLP-1) mimetics and analogues (eg, Exendin); androgens (eg, dehydroepiandrosterone and derivatives such as etiocholandione), testosterone, anabolic steroids (eg, oxandrolone), and steroidal hormones; galanin receptor antagonists; cytokine agents such as ciliary neurotrophic factor; amylase inhibitors; enterostatin agonists/mimetics; orexin/hypocretin antagonists; urocortin antagonists; bombesin agonists; modulators of protein kinase A; corticotropin-releasing factor mimetics; cocaine- and amphetamine-regulated transcript mimetics; calcitonin-gene related peptide mimetics; and fatty acid synthase inhibitors.

Add-on therapy using Compounds of Formula I:

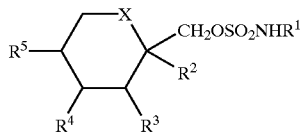

(I)

has not, however, yet been contemplated in the art.

Such compounds are structurally novel antiepileptic compounds that are highly effective anticonvulsants in animal tests (MARYANOFF, B. E, NORTEY, S. O., GARDOCKI, J. F., SHANK, R. P. AND DODGSON, S. P. *J. Med. Chem.* 1987, 30, 880–887; MARYANOFF, B. E., COSTANZO, M. J., SHANK, R. P., SCHUPSKY, J. J., ORTEGON, M. E., AND VAUGHT J. L. *Bioorg. Med. Chem. Lett.* 1993, 3, 2653–2656; SHANK, R. P., GARDOCKI, J. F., VAUGHT, J. L., DAVIS, C. B., SCHUPSKY, J. J., RAFFA, R. B., DODGSON, S. J., NORTEY, S. O., MARYANOFF, B. E. *Epilepsia* 1994, 35, 450–460; MARYANOFF B E, COSTANZO M J, NORTEY S O, GRECO M N, SHANK R P, SCHUPSKY J J, ORTEGON M P, VAUGHT J L. *J. Med. Chem.* 1998, 41, 1315–1343). These compounds are covered by three U.S. Pat. No. 4,513,006, No. 5,242,942, and No. 5,384,327. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., *Epilepsia* 1995, 36 (S4), 33; S. K. SACHDEO, R. C. SACHDEO, R. A. REIFE, P. LIM and G. PLEDGER, *Epilepsia* 1995, 36 (S4), 33; T. A. GLAUSER, *Epilepsia* 1999, 40 (S5), S71–80; R. C. SACHDEO, *Clin. Pharmacokinet.* 1998, 34, 335–346), and is currently marketed for the treatment of seizures in patients with simple and complex partial epilepsy and seizures in patients with primary or secondary generalized seizures in the United States, Europe and most other markets throughout the world. Despite the fact that topiramate, having the brand name Topomax® is widely marketed it has not been used on an add-on therapy with anti-diabetic agents for treating Type II Diabetes Mellitus or Syndrome X.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., *Epilepsia* 1994, 35, 450–460). Subsequent studies revealed that Compounds of Formula I were also highly effective in the MES test in rats. Topiramate was also found to effectively block seizures in several rodent models of epilepsy (J. NAKAMURA, S. TAMURA, T. KANDA, A. ISHII, K. ISHIHARA, T. SERIKAWA, J. YAMADA, and M. SASA, *Eur. J. Pharmacol.* 1994, 254, 83–89), and in an animal model of kindled epilepsy (A. WAUQUIER and S. ZHOU, *Epilepsy Res.* 1996, 24, 73–77).

More recently compounds of formula I have been found to be effective for maintaining weight loss and in the treatment of obesity, as disclosed in U.S. Pat. No. 6,071,537 (WO 9800130). Thakur et al in WO9944581 disclose the use of topiramate for the treatment of diabetes.

DISCLOSURE OF THE INVENTION

It has now been found that compounds of the following formula (I):

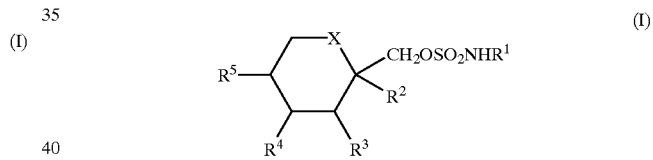

(I)

wherein X is O or CH$_2$, and R$^1$, R$^2$, R$^3$, R$^4$ and R$^5$ are as defined herein when administered in combination with one or more anti-diabetic agents, as defined herein, are useful in the treatment of Type II Diabetes Mellitus and Syndrome X.

DETAILED DESCRIPTION OF THE PREFERRED EMBODIMENTS

The sulfamates of the invention are of the following formula (I):

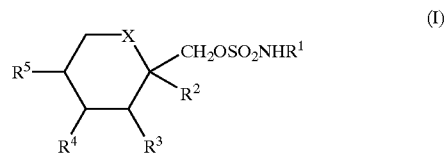

(I)

wherein
X is CH$_2$ or oxygen;
R$^1$ is hydrogen or alkyl; and
R$^2$, R$^3$, R$^4$ and R$^5$ are independently hydrogen or lower alkyl and, when X is CH$_2$, R$^4$ and R$^5$ may be alkene groups joined to form a benzene ring and, when X is oxygen, $R^2$ and $R^3$ and/or $R^4$ and $R^5$ together may be a methylenedioxy group of the following formula (II):

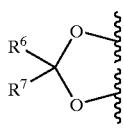

(II)

wherein $R^6$ and $R^7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R^2$, $R^3$, $R^4$, $R^5$, $R^6$ and $R^7$ are of about 1 to 3 carbons and include methyl, ethyl, iso-propyl and n-propyl. When X is $CH_2$, $R^4$ and $R^5$ may combine to form a benzene ring fused to the 6-membered X-containing ring, i.e., $R^4$ and $R^5$ are defined by the alkatrienyl group =C—CH=CH—CH=.

A particular group of compounds of formula (I) is that wherein X is oxygen and both $R^2$ and $R^3$ and $R^4$ and $R^5$ together are methylenedioxy groups of the formula (II), wherein $R^6$ and $R^7$ are both hydrogen both alkyl or combine to form a spiro cyclopentyl or cyclohexyl ring, in particular where $R^6$ and $R^7$ are both alkyl such as methyl. A second group of compounds is that wherein X is $CH_2$ and $R^4$ and $R^5$ are joined to form a benzene ring. A third group of compounds of formula (I) is that wherein both $R^2$ and $R^3$ are hydrogen.

The compounds of formula (I) may be synthesized by the following methods:

(a) Reaction of an alcohol of the formula $RCH_2OH$ with a chlorosulfamate of the formula $ClSO_2NH_2$ or $ClSO_2NHR^1$ in the presence of a base such as potassium t-butoxide or sodium hydride at a temperature of about −20° to 25° C. and in a solvent such as toluene, THF, or dimethylformamide wherein R is a moiety of the following formula (III):

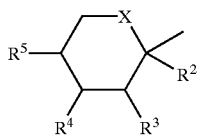

(III)

(b) Reaction of an alcohol of the formula $RCH_2OH$ with sulfurylchloride of the formula $SO_2Cl_2$ in the presence of a base such as triethylamine or pyridine at a temperature of about −40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R^1NH_2$ at a temperature of abut 40° to 25° C. in a solvent such as methylene chloride or acetonitrile to produce a compound of formula (I). The reaction conditions for (b) are also described by T. Tsuchiya et al. in *Tetrahedron Lett.*, 1978, 3365.

(c) Reaction of the chlorosulfate $RCH_2OSO_2Cl$ with a metal azide such as sodium azide in a solvent such as methylene chloride or acetonitrile yields an azidosulfate of the formula $RCH_2OSO2N_3$ as described by M. Hedayatullah in *Tetrahedron Lett.* 1975, 2455. The azidosulfate is then reduced to a compound of formula (I) wherein $R^1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R^2$ and $R^3$ and $R^4$ and $R^5$ are identical and are of the formula (II) may be obtained by the method of R. F. Brady in *Carbohydr. Res.* 1970, 14, 35 or by reaction of the trimethylsilyl enol ether of a $R^6COR^7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al. in *J. Org. Chem.* 1973, 38, 3935.

Further, carboxylic acids and aldehydes of the formulae RCOOH and RCHO may be reduced to compounds of the formula $RCH_2OH$ by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in "Modern Synthetic Reactions", 2nd Ed., pages 45 to 144 (1972).

The compounds of formula I may also be made by the process disclosed U.S. Pat. No. 4,513,006, No. 5,242,942, and No. 5,384,327, which are incorporated by reference herein.

The compounds of formula I include the various individual isomers as well as the racemates thereof, e.g., the various alpha and beta attachments, i.e., below and above the plane of the drawing, of $R^2$, $R^3$, $R^4$ and $R^5$ on the 6-membered ring. Preferably, the oxygen of the methylenedioxy group (II) are attached on the same side of the 6-membered ring.

Anti-diabetic agents useful for the treatment of Type II diabetes mellitus and Syndrome X include, but are not limited to, sulfonylureas, meglitinides, agents which modify insulin secretion, biguanides, thiazolidinediones, PPAR-gamma agonists, Retinoid-X receptor (RXR) modulators, insulin sensitizing agents, alpha-glucosidase inhibitors, insulins, small molecule mimics of insulin, Na-glucose co-transporter inhibitors, amylin agonists, glucagon antagonists, and the like.

Suitable examples of anti-diabetic agents include, chlorpropamide, tolazamide, tolbutamide, glyburide, glipizide, glimepiride, repaglinide, metformin, rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, GW2570, targretin, 9-cis-retinoic acid, ascarbose, miglitol, L-783281, TE-17411, T-1095, BAY-279955, phlorizen, pramlintide, regular-acting insulin, short-acting insulin, intermediate-acting insulin, long-acting insulin, inhaled insulin, insulin analogues, acetohexamide, buformin, glibornuride, glyhexamide, glymidine, linogliride, palmoxirate, zopolrestat; etoformin, gllicalzide, glypinamide, and the like.

In addition to antidiabetic agents, add-on therapeutic agents may include anti-obesity agents such as orlistat, sibutramine, mazindol, benzphetamine, phenmetrazine, phentermine, diethylpropion, mazindol, sibutramine, phenylpropanolamine, ephedrine, quipazine, fluoxetine, sertraline, fenfluramine, dexfenfluramine, apomorphine, Exendin, dehydroepiandrosterone, etiocholandione, testosterone, oxandrolone, and the like. In addition, therapies may also include add-on treatment with anti-hypertensive agents and/or hypolipidemic agents.

As used herein, the terms "Syndrome X", "Metabolic Syndrome" and "Metabolic Syndrome X" shall mean a disorder that presents risk factors for the development of Type II diabetes mellitus and cardiovascular disease and is characterized by insulin resistance and hyperinsulinemia and may be accompanied by one or more of the following:

(a) glucose intolerance, (b)Type II diabetes, (c)dyslipidemia, (d) hypertension and (e) obesity.

The ability of the compounds of formula I administered in combination with an anti-diabetic agent to treat Type II diabetes mellitus and Syndrome X is based on the following case studies.

EXAMPLE 1

Case Study A (PT #2 ES)

The patient was a 59 year old female with a 6 year history of Type II diabetes. For the past four years the patient was being treated with insulin (70/30). At the start of treatment patient's weight was 236 lbs, measured cholesterol was 316 mg/dl and measured glucose was 166 mg/dl. The patient was started on Topiramate for treatment of seizures and titrated to 75 mg a day. After 2 months of treatment, the patient indicated that her blood sugar had improved significantly to where she was using the insulin less often. After 11 months, topiramate dosage was increased to 200 mg b.i.d. After one year, the patient's weight was 225 lbs and Hbg A1C was 6.94%. After 16 months, patient's fasting glucose was 89 mg/dl. After 18 months, patients indicated that home measured blood sugars were consistently less than 120 mg/dl, whereas previously blood sugars ranged between 150 and 160 mg/dl.

EXAMPLE 2

Case Study B (PT#3)

The patient was a 76 year old male with a 5 year history of Type II diabetes. At the start of treatment, patient was taking 40 mg/day Glucotrol (glipizide, a sulfonylurea) and weighed 293 lbs. The patient was titrated on topiramate to 50 mg/day. After 1 month of treatment, patient reported that home measured blood sugars had dropped from a baseline of 300 mg/dl to measured blood sugars of 140 mg/dl. After 2 months, the patient indicated average blood sugar levels of 80–140 mg/dl and weight loss to 272 lbs.

EXAMPLE 3

Case Study C (PT #5 CL)

The patient was a 69 year old male with an 8 year history of diabetes. Prior to treatment, patient's weight was 201 lbs, Hgb A1C was 9.3% and blood sugar was 309 mg/dl. Patient was taking Glucophage (metformin hydrochloride) at four 500 mg tablets/day (2 tablets in the morning, 1 tablet in the afternoon and 1 tablett at night, for a total of 2000 mg/day), DiaBeta (glyburide) at at 10 mg twice a day (total of 20 mg/day) and Rezulin (troglitazone) at 200 mg/day. Patient was started on topiramate at 75 mg b.i.d (150 mg/day). Patient indicated that blood sugars were "doing better". Topiramate dosage was increased to 150 mg b.i.d (300 mg/day). at which time the patient was able to stop Glucophage due to improved sugar control. After 15 months patient's weight was 190 lbs with blood sugars controlled on 100 mg topiramate in the morning, 200 mg topiramate at night (Total of 300 mg/day), DiaBeta at 10 mg twice a day and Rezulin at 200 mg once a day.

EXAMPLE 4

Case Study D (PT #6 WD)

The patient was a 62 year old female, with a history of elevated blood sugars and a weight of 188 lbs. At the time of initial treatment, patient's blood sugar was 426 mg/dl. Patient was started on topiramate, titrated to 100 mg once a day. The patient was also prescribed Amaryl (glimepiride). After 3 months, patient's blood sugar averaged in the upper 100s, lab sugars measured at 138 mg/dl, cholesterol at 278 mg/dl, triglycerides at 212 mg/dl and HgbA1C at 6.7%. After one year, topiramate dosage was increased to 200 mg/day with lab measured blood sugars at 141 mg/dl, cholesterol at 200 mg/dl and triglycerides at 500 mg/dl. Patient weighed 160 lbs. Patient was able to stop taking the Amaryl due to improved sugar control. Due to concerns about weight loss, topiramate was decreased to 100 mg/day. After 21 months, patient's weight was 170 lbs, blood sugars were reported doing well. Lab measured glucose was 115 mg/dl, cholesterol was measured at 236 mg/dl, triglycerides at 106 mg/dl and HgbA1C at 5.7%.

The above studies show that the oral administration of topiramate in combination with an anti-diabetic agent consistently improved the status of markers of diabetes mellitus, including blood glucose, glycosylated hemoglobin (Hgb A1C), and triglyceride levels.

Thus, for treating Type II diabetes mellitus or Syndrome X, a compound of formula I in combination with an anti-diabetic agent or agents may be employed comprising administering repeated oral doses of the compound of formula I in the range of about 25 to 300 mg once or twice daily and repeated doses of the anti-diabetic agent or agents at therapeutically effective dosages. The therapeutically effective dosage for anti-diabetic, anti-hypertensive and hypolipidemic agents disclosed herein may be readily determined by those skilled in the art based on standard dosage guidelines.

As used herein, unless otherwise noted, the term "therapeutically effective amount", means that amount of active compounds or pharmaceutical agents that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to the administration of a combination of one or more anticonvulsant derivatives and one or more anti-diabetic or other pharmacological agents, "therapeutically effective mount" shall mean that amount of the combination of agents taken together so that the combined effect elicits the desired biological or medicinal response. For example, the therapeutically effective amount of combination therapy comprising administration of a compound of formula (I) and an anti-diabetic agent would be the amount of the compound of formula (I) and the amount of the anti-diabetic agent that when taken together or sequentially have a combined effect that is therapeutically effective. Further, it will be recognized by one skilled in the art that in the case of combination therapy with a therapeutically effective amount, as in the example above, the amount of the compound of formula (I) and/or the amount of the anti-diabetic agent individually may or may not be therapeutically effective.

Wherein the present invention is directed to the administration of a combination, the compounds may be co-administered by any suitable means, simultaneously, sequentially or in a single pharmaceutical composition. Where the compounds are administered separately, the number of dosages of each compound given per day, may not necessarily be the same, e.g. where one compound may have a greater duration of activity, and will therefore, be administered less frequently.

The compound(s) of formula (I) and the anti-diabetic agent(s) may be administered via the same or different routes of administration. The compound(s) of formula (I) and the anti-diabetic agent(s) may be administered via the same or different routes of administration. Suitable examples of methods of administration are orally, intravenous (iv), intramuscular (im), and subcutaneous (sc). Compounds may also be administrated directly to the nervous system including, but not limited to the intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula (I) and the anti-diabetic agent(s) may be administered according to simultaneous or alternating regimens, at the same or different times during the course of the therapy, concurrently in divided or single forms.

Optimal dosages to be administered may be readily determined by those skilled in the art, and will vary with the particular compound used, the mode of administration, the strength of the preparation and the advancement of the disease condition. In addition, factors associated with the particular patient being treated, including patient's sex, age, weight, diet, time of administration and concomitant diseases, will result in the need to adjust dosages.

As used herein, the term "composition" is intended to encompass a product comprising the specified ingredients in the specified amounts, as well as any product which results, directly or indirectly, from combinations of the specified ingredients in the specified amounts.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., i.v. sterile injectable formulations will be prepared using appropriate solubilizing agents. A unit dose would contain about 15 to 200 mg of the active ingredient. Topiramate is currently available for oral administration in round tablets containing 25 mg, 100 mg or 200 mg of active agent. The tablets contain some or all of the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for treating Type II diabetes mellitus in mammals afflicted with such condition comprising administering to said mammal a therapeutically effective amount of a compound of the formula I:

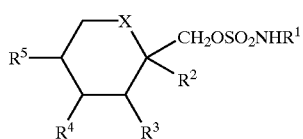

(I)

wherein

X is $CH_2$ or oxygen;

$R^1$ is hydrogen or alkyl; and $R^2$, $R^3$, $R^4$ and $R^5$ are independently hydrogen or lower alkyl and, when X is $CH_2$, $R^4$ and $R^5$ may be alkene groups joined to form a benzene ring and, when X is oxygen, $R^2$ and $R^3$ and/or $R^4$ and $R^5$ together may be a methylenedioxy group of the following formula (II):

(II)

wherein $R^6$ and $R^7$ are the same or different and are hydrogen, lower alkyl or are alkyl and are joined to form a cyclopentyl or cyclohexyl ring;

in combination with a therapeutically effective amount of one or more anti-diabetic agent.

2. The method of claim 1 wherein the compound of formula I is topiramate.

3. The method of claim 1, wherein the therapeutically effective amount of the compound of formula I is from about 32 to 512 mg.

4. The method of claim 1, wherein the therapeutically effective amount of the compound of formula I is of from about 16 to 256 mg once or twice daily.

5. The method of claim 1 wherein the anti-diabetic agent is selected from the group consisting of a sulfonylurea, a meglitinide, an agents which modify insulin secretion, a biguanide, a thiazolidinedione, a peroxisome proliferator-activated receptor-gamma agonist (PPAR-gamma), a Retinoid-X receptor (RXR) modulator, an insulin sensitizing agent, an alpha-glucosidase inhibitor, an insulin, a small molecule mimics of insulin, Na a-glucose co-transporter inhibitor, an amylin agonists and a glucagon antagonist.

6. The method of claim 1 wherein the anti-diabetic agent is selected from the group consisting of metformin, a sulfonylureas, a thiazolidinediones and insulin.

7. A method of treating Syndrome X (Insulin Resistance Syndrome, Metabolic Syndrome, or Metabolic Syndrome X) in mammals afflicted with such condition comprising administering to said mammal a therapeutically effective amount of a compound of the formula I:

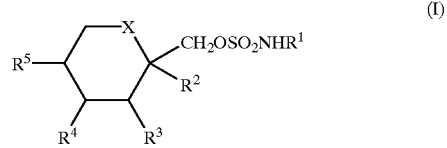

(I)

wherein

X is $CH_2$ or oxygen;

$R^1$ is hydrogen or alkyl; and $R^2$, $R^3$, $R^4$ and $R^5$ are independently hydrogen or lower alkyl and, when X is $CH_2$, $R^4$ and $R^5$ may be alkene groups joined to form a benzene ring and, when X is oxygen, $R^2$ and $R^3$ and/or $R^4$ and $R^5$ together may be a methylenedioxy group of the following formula (II):

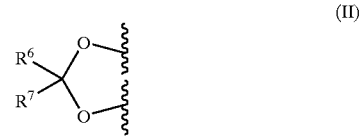

(II)

wherein $R^6$ and $R^7$ are the same or different and are hydrogen, lower alkyl or are alkyl and are joined to form a cyclopentyl or cyclohexyl ring;

in combination with a therapeutically effective amount of one or more anti-diabetic agent.

8. The method of claim 7, wherein the compound of formula I is topiramate.

9. The method of claim 7, wherein the therapeutically effective amount of the compound of formula I is from about 32 to 512 mg.

10. The method of claim 7, wherein the therapeutically effective amount of the compound of formula I is of from about 16 to 256 mg once or twice daily.

11. The method of claim 7 wherein the anti-diabetic agent is selected from the group consisting of a sulfonylurea, a meglitinide, an agents which modify insulin secretion, a biguanide, a thiazolidinedione, a peroxisome proliferator-activated receptor-gamma agonist (PPAR-gamma), a Retinoid-X receptor (RXR) modulator, an insulin sensitizing agent, an alpha-glucosidase inhibitor, an insulin, a small molecule mimics of insulin, Na a-glucose co-transporter inhibitor, an amylin agonists and a glucagon antagonist.

12. The method of claim 7 wherein the anti-diabetic agent is selected from the group consisting of metformin, a sulfonylureas, a thiazolidinediones and insulin.

* * * * *